(12) United States Patent
Ruiz-Roso Calvo De Mora et al.

(10) Patent No.: US 7,393,551 B2
(45) Date of Patent: Jul. 1, 2008

(54) DENATURED CAROB FLOUR (DCF) WITH A LOW CONTENT OF SOLUBLE TANNINS AND SUGARS, MEANT FOR HUMAN CONSUMPTION AND PROCESS TO OBTAIN IT

(75) Inventors: Baltasar Ruiz-Roso Calvo De Mora, Madrid (ES); Ana Maria Requejo Marcos, Madrid (ES); Lourdes Perez-Olleros Conde, Madrid (ES); Metodio Martin Casero, Madrid (ES); Bernd Haber, Mainz (DE)

(73) Assignee: Investigacion Y Nutricion, S.L., Madrid (ES)

( * ) Notice: Subject to any disclaimer, the term of this patent is extended or adjusted under 35 U.S.C. 154(b) by 591 days.

(21) Appl. No.: 10/522,512

(22) PCT Filed: Aug. 5, 2003

(86) PCT No.: PCT/EP03/08636

§ 371 (c)(1),
(2), (4) Date: Jan. 27, 2005

(87) PCT Pub. No.: WO2004/014150

PCT Pub. Date: Feb. 19, 2004

(65) Prior Publication Data

US 2006/0003063 A1 Jan. 5, 2006

(30) Foreign Application Priority Data

Aug. 6, 2002 (ES) .................................. 200201865

(51) Int. Cl.
*A23L 1/015* (2006.01)
(52) U.S. Cl. .................. 426/615; 426/622; 426/648; 426/455; 426/456; 426/460; 426/463; 426/464; 426/465; 426/466; 426/469
(58) Field of Classification Search ................. 426/615, 426/648, 455, 456, 460, 463, 464, 465, 466, 426/469, 622
See application file for complete search history.

(56) References Cited

U.S. PATENT DOCUMENTS

| | | | |
|---|---|---|---|
| 4,617,188 A * | 10/1986 | Page et al. .................. 424/658 |
| 4,999,197 A | 3/1991 | Wuersch .................. 424/195.1 |
| 5,043,160 A * | 8/1991 | Wursch .................. 424/757 |
| 5,330,755 A | 7/1994 | Remi .................. 424/195.1 |
| 5,624,500 A | 4/1997 | Sanjuan Diaz ................ 127/30 |
| 5,856,313 A | 1/1999 | Marco et al. .................. 514/22 |

OTHER PUBLICATIONS

Pulido R, Bravo L, Saura-Calixto F. *Carob Bean in food and Feed: Current Status and Future Potentials—A Critical Appraisal.* Journel of Food Science and Technology, Association of Food Scientists and technologist, US vol. 33, No. 5, 1996, pp. 365-383, XP00901522.
R. Pulido et al., *Antioxidant activity of dietary polyphenols as determined by a modified ferric reducing/antioxidant power assay*; J Agric Food Chem (2000) vol. 48, No. 8, pp. 3396-3402.
Beatrice L.Pool-Zobel et al., *Isoflavonoids and lignans have different potentials to modulate oxidative genetic damage in human colon cells*; Carcinogenesis (2000) vol. 21, No. 6, pp. 1247-1252.
Richard Perez et al., *Sodium butyrate upregulates Kupffer cells PGE-2 production and modulates immune function*; J. Surgical Research (1998) vol. 78, pp. 1-6.
Beong Ou Lim et al., *Dietary fibres modulate indices of intestinal immune function in rats*; J. Nutr. (1997) vol. 127, pp. 663-667.
Yoshihiro Sowa et al., *Butyrate as a model for gene-regulating chemoprevention and chemotherapy*; BioFactors (2000), vol. 12 (1-4) pp. 283-287.
P. Perrin et al., *Only fibers promoting a stable butyrate producing colonic ecosystem decrease the rate of aberrant crypt foci in rats*; Gut. (2001) vol. 48, No. 1, pp. 53-61.
Sarah Bates et al., Insulin-like effect of pinitol; British Journal of Pharmacology (2000) vol. 130, No. 8. pp. 1944-1948.
V. L. Singleton et al., *Colorimetry of total phenolics with phosphomolybdicphosphotungstic acid reagents*; Am. J. Enol. Vitic (1965) vol. 16, pp. 144-158.
Ann E. Hagerman et al., *Methods for determination of condensed and hydrolyzable tannins*; In F. Shahidi (Ed), Antinutrients and phytochemicals in foods (pp. 209-222; ACS symposium Series 662. Washington, DC. American Chemical Society.

* cited by examiner

*Primary Examiner*—Helen F Pratt
(74) *Attorney, Agent, or Firm*—ProPat, L.L.C.

(57) ABSTRACT

The present invention provides an improved denatured carob flour, which includes 2 to 15% sugars, 0.2 to 1.5% cyclitols (pinitol), 2 to 10% lignins, 10 to 30% celluloses, 3 to 20% hemicelluloses, 1 to 6% pectins, 25 to 55% condensed tannins, 3 to 9% protein and less than 8% water. The invention further provides a process to obtain a denatured carob flour that includes the following steps: a. cleaning the whole fruit; b. crushing the carob fruits; c. separating the carob seeds and kibbled carob pulp, d. toasting between 130 to 200° C.; e. an extracting process; f. separating; g. milling 90% of particles below 250 pm; h. separating; i. drying below 8%; and j. classifying (sieving).

26 Claims, No Drawings

DENATURED CAROB FLOUR (DCF) WITH A LOW CONTENT OF SOLUBLE TANNINS AND SUGARS, MEANT FOR HUMAN CONSUMPTION AND PROCESS TO OBTAIN IT

CROSS REFERENCE TO RELATED APPLICATIONS

This application is being filed under Rule 1.371 as a National Stage Application of International Application No. PCT/EP2003/008636 filed Aug. 5, 2003, which claims priority to parent Spanish Patent Application No. 200201865 filed Aug. 6, 2002. The parent application, Spanish Patent Application No. 200201865, and associated international application, Application No. PCT/EP2003/008636, are both hereby incorporated by reference herein in their entirety.

FIELD OF THE INVENTION

Denatured carob flour and the process to obtain it described in this specification will be applied in industry to develop dietary fiber products rich in condensed tannins for human consumption.

DESCRIPTION OF PRIOR ART

There is considerable interest in developing dietary fiber products rich in polyphenol compounds owing to the known protective role of these substances against cardiovascular disease by reducing hypercholesterolemia and their effects on the efficacy of the intestinal translocation and the prevention of colonic cancer.

Hence, to cite some studies from the literature, polyphenolic compounds present in different concentrations in dietary fiber and in different food compounds have important antioxidant effects (Pulido R, Bravo L, Saura-Calixto F. *Antioxidant activity of dietary polyphenols as determined by a modified ferric reducing/antioxidant power assay*. J. Agric Food Chem (2000) 48(8): 3396-402), that can be used to prevent and treat certain diseases including cancer (Pool-Zobel B L, Adlercreutz H, Glei M, Liegibel U M, Sittlingon J., Rowland I., Wahala K, Rechkemmer G. *Isoflavonoids and lignans have different potentials to modulate oxidative genetic damage in human colon cells*). Carcinogenesis (2000) 21(6): 1247-52). Nevertheless, there is only a small amount of condensed tannins in the different dietary fibers and products enriched in these natural polyphenols cannot be used in the chronic treatment of degenerative diseases because at these levels they have a strong astringent and antinutritional effect.

On the other hand, pectins, gums and other similar products, majority components of soluble fibers, although substances produced by their colonic fermentation (e.g. butyrate) have been found to have potentially therapeutic applications, important benefits for the immune system (Perez R. Stevenson f. Jhonson J., Morgan M., Ericson K. Hubbard N. E. Morand L. Ruduch S., Kaztnelson S. *Sodium butyrate upregulates Kupffer cells PGE-2 production avid modulates immune function*. J. Surg. Res. (1998) 78, 1-6; Lim B. O. Yamada K. Nonaka M. Kuramoto Y., Hung P., Sugano M. *Dietary fibres modulate indices of intestinal immune function in rats*. J. Nutr. (1997) 127, 663-7.) and in the prevention of colonic cancer in cell culture studies (Sowa Y, Sakai T. *Butyrate as a model for "gene-regulating chemoprevention and chemotherapy"* biofactors (2000); 12 (1-4): 283-7), in human trials the results are not as clear, probably because they ferment rapidly in the proximal colon and little butyrate arrives at the distal colon, the most common site of neoplasic processes (Perrin P, Pierre F, Patry Y, Champ M, Berreur M, Pardal G, Bornet F, Meflah K, Menanteau J. *Only fibers promoting a stable butyrate producing colonic ecosystem decrease the rate of aberrant crypt foci in rats*. Gut. (2001) 48(1): 53-61). Nevertheless, mainly because of economic interest in animal production, the delaying effect of tannins on bacterial fermentation in the digestive tract is currently well known. Therefore, in suitable quantities they can regulate and delay the production of butyrate in the final portions of the colon and rectum.

SUMMARY OF THE INVENTION

Carob pulp is also rich in cyclitol and pinitol, a product that is transformed into inositol in the organism, a molecule of great interest for cell metabolism control (Bates S H, Jones R B, Bailey C J. *Insulin-like effect of pinitol*. Br J Pharacol (2000) 130 (8): 1944-48). The object of the present invention is, therefore, to eliminate from the carob pulp a large proportion of its sugars and soluble tannins, but maintaining a significant pinitol contents and to modify its condensed tannins to maintain its beneficial effects (hypolipaemic activity), regulators of intestinal function, antioxidants etc), eliminate its astringent and antinutritional effects and to be able to use in this way the product as a dietary product for human or animal use, as well as a component in pharmaceuticals.

DESCRIPTION OF THE INVENTION

The denatured carob flour with low soluble tannin and sugar contents, described here, has the following composition, depending on the variety of fruit used:

Sugars . . . usually 2-15%, typically 3-10%
Cyclitols (pinitol) . . . usually 0.2-1.5%; typically 0.3-1%
Lignins . . . usually 2-10% ; typically 2-7%
Celluloses . . . usually 10-30% ; typically 15-28%
Hemicelluloses . . . usually 3-20% ; typically 3-9%
Pectins . . . usually 1-6%; typically 2-5%
Condensed tannins . . . usually 25-55%; typically 30-48%
Protein . . . usually 3-9%; typically 4-8%
Water contents less than . . . usually below 8%; typically below 6%

All percentages given are weight percentages (wt.-%) if not stated otherwise.

This carob flour is characterized by having an active ingredient with at least 25%, usually 30%, typically 40% of condensed carob tannins denatured thermally with a weight ratio of soluble to insoluble polyphenols less than 0.05 (solubility determined with water at 37° C.). Evaluation of the polyphenol contents has been carried out by first determining the soluble tannin contents in water at 37° C. stirring for 15 minutes; these are determined spectrophotrometrically in this water with the Folin-Ciocalteau reagent (Singleton V. L. Rossi J. A. *Colonimetry of total phenolics with phosphomolybdicphosphotungstic acid reagents*. Am. J. Enol. Vitic (1965). 16:144-158). The insoluble polyphenols of the residue are determined by treatment with HCl-butanol according to the method of Hagerman and coworkers (Hagerman A. E. Zhao Y. Jonson S. *Methods for determination of condensed and hydrolyzable tannins*. In F. Shahidi (Ed), Antinutrients and phytochemicals in foods (p. 209-222). ACS symposium Series 662. Washington, D.C. American Chemical Society).

In this invention, carob pulp, rich in condensed tannins, formed by polymerization of flavan-3-ol and its gallic esters with a strong astringent effect, are treated with heat (between usually 130 and 200° C., typically 140 and 150° C.) to result in a change of structure of the polyphenols with partial degradation and polymerization and to eliminate astringency and interference with absorption of nutrients in the diet but maintaining most of its positive effects. It can, therefore, be used for human diet and nutrition (as ordinary foods, enriched foods, dietary foods, foods for special medical purposes or dietary supplements), without antinutritional problems, while the effects of these condensed tannins as a sequesterant of cholesterol and bile salts, as antioxidants, laxatives and regulators of intestinal fermentation are maintained. Furthermore applications in animal feed and pet food or in human and animal pharmaceuticals are possible.

The process to obtain the previously described carob flour consists in a series of steps, as follows:

a. Cleaning the whole fruit: Cleaning includes e.g. dry (e.g. mechanical separation of contaminants) or wet (e.g. wash out with water) cleaning steps. Dependent on the cleaning procedure this step may additionally include a drying step. This could be done e.g. in an air flow.

b. Crushing the carob fruits: this could be done, e.g. by passing the carob fruit through a mill, typically a hammer mill, to shred the pods to pieces smaller than 3 cm.

c. Separation of carob seeds and kibbled carob pulp: the seed can be separated using a sieve with a suitably sized mesh, depending on the conditions of the process, the agronomical variety and the water contents of the fruit. As an alternative suitable process air classification or other mechanical or physical technologies can be used.

d. Toasting (modification of the structure of condensed tannins): this process is important to change the nutritional properties of the condensed tannins. This can be reached by toasting of the carob kibbles at temperatures usually between 130-200° C., typically between 140-150° C. for a certain time period depending on the water content of the pulp and the particle size. Usual time periods for this toasting process are 5-60 minutes, typically 10-20 minutes.

e. Extraction process: the toasted carob pulp is extracted with water or any other suitable solvent to remove the sugars and water-soluble tannins. The ratio of extraction material to solvent is usually higher than 1:20 (by weight), typically 1:4 (by weight). The extraction can be made at different temperatures usually in the range of 5-80° C., typically between 20-55° C. Extraction can be done e.g. in a simple extraction tank (with or without stirrer) or in a continuously operating extractor (counter current flow extraction). Dependent on the other extraction parameters extraction time usually lies between 5 minutes to 24 hours, typically between 15 minutes and 2 hours.

f. Separation: Separation of the water soluble components from the water insoluble parts can be done by several techniques including decantation, filtration, or centrifugation.

g. Milling: the water-insoluble residue is ground to a fine powder by milling techniques. Preferred equipment is a colloidal mill, but also other milling techniques can be considered (e.g. ball mills). Reached particle sizes are below 250 µm (90% of particles below 250 µm), usually below 150 µm (90% of particles below 150 µm) and typically below 100 µm (90% of particles below 100 µm).

h. Optionally repetition of steps e. (extraction) and f. (separation) to further reduce the water soluble constituents in the obtained residue. Two further extraction steps are sufficient to reach sugar contents usually below 15% and typically below 10% in the insoluble residue.

i. Separation: After the last extraction step the obtained residue is pressed, filtered, decanted, or centrifuged to eliminate as much as possible of the water.

j. Drying: To reduce the water content usually below 8%, typically below 6%. This can be managed by several drying techniques including a drying oven, spray drying, vacuum drying, drying in an air or inert gas stream. Temperatures should usually not lie above 140° C., typically not above 60-65° C.

k. Classification (sieving): dependent on the application the obtained product can be sieved to obtain standardized particle size limits.

The whole production process, as described above in the steps a-k, or parts of it, can also be done in a continuous way.

The properties of this denatured carob flour: hypocholesterolemiant, regulator of gastrointestinal dynamics, bile salt chelant and antioxidant on which we base its potential dietary and pharmacological applications for both human and animals, have been demonstrated in a number of animal trials carried out in the Department of Nutrition of the Universidad Complutense de Madrid, of which we summarize some relevant results.

First of all, in experimental animals the influence of this denatured carob flour (DCF) on ingestion, weight increase, growth, fecal volume, fecal polyphenol and butyrates was studied. To do this, a total of three batches of 10 growing rats were fed isocaloric synthetic diets modified to suit their nutritional requirements in which the only variable was the type of dietary fiber used: 2% apple pectin in all batches as butyrate source and 5% in batch 1 of microcrystalline cellulose (Avicel R), 5% in batch 2 of carob fiber (NCF=Natural Carob Fibre) and 5% in batch 3 of DCF. It was found that intake of DCF did not affect weight increase in animals or the dietary efficacy of the diets compared to cellulose and it can, therefore, be concluded that the treatment has managed to eliminate the antinutritive effect of its condensed tannins, while the carob fiber (NCF), slightly but significantly reduces both parameters. The DCF increases fecal volume and weight compared to cellulose and results in a similar fecal volume and weight, at the same doses, as NCF, but with fecal butyrate and polyphenol concentrations 30% and 10% higher, respectively, in rats fed with our invention than in those fed with diets containing carob fiber (NCF), hence, as repeatedly described by several authors, protection against the formation of mutagenic or carcinogenic compounds (electrophylic molecules) in animals that consume DCF is higher than that achieved with carob fibers (NCF).

To determine its effects on blood lipids, 30 young rats with experimental hypercholesterolemia were used (total cholesterol 235 mg/dl), 5 groups with 10 rats each were formed and the following fiber sources were added to their diets:

Batch 1-10% cellulose

Batch 2-10% carob fiber (NCF)

Batch 3-10% carob flour (DCF)

After three weeks of treatment mean serum cholesterol levels were:

Batch 1: 285 mg/dl

Batch 2: 165 mg/dl

Batch 3-112 mg/dl

The conclusions of this study can be summarized as follows:

Taking into account that the cellulose used had no effect on cholesterolemia and that our invention (DCF) produced, significantly (p<0.05), the greatest reduction in serum cholesterol levels in animals, we can conclude that our invention has a more pronounced effect on cholesterolemia than natural carob fibers (NCF). This effect seems to be mediated by more sequestration of bile salts by DCF.

The percentages, temperatures and other additional factors associated with the product and with the process described can be variable provided that they are additional and secondary and do not alter the essence of the patent described here.

The invention claimed is:

1. Denatured carob flour comprising
   sugars in an amount of 2 to 15% by weight,
   cyclitols in an amount of 0.2 to 1.5% by weight,
   lignins in an amount of 2 to 10% by weight,
   celluloses in an amount 10 to 30% by weight,
   hemicelluloses in an amount of 3 to 20% by weight,
   pectins in an amount of 1 to 6% by weight,
   denatured condensed tannins in an amount of 25 to 55% by weight,
   protein in an amount of 3 to 9% by weight and
   water in an amount of less than 8% by weight.

2. Denatured carob flour according to claim 1, wherein the sugar is in an amount of between 3 to 10% by weight.

3. Denatured carob flour according to claim 1, wherein the cyclitols is are in an amount of between 3 to 1% by weight.

4. Denatured carob flour according to claim 1, wherein the lignins are in an amount of between 2 to 7% by weight.

5. Denatured carob flour according to claim 1, wherein the celluloses are in an amount of between 15 to 28% by weight.

6. Denatured carob flour according to claim 1, wherein the hemicelluloses are in an amount of between 3 to 9% by weight.

7. Denatured carob flour according to claim 1, wherein the pectins are in an amount of between 2 to 5% by weight.

8. Denatured carob flour according to claim 1, wherein the condensed tannins are in an amount of between 30 to 48% by weight.

9. Denatured carob flour according to claim 1, wherein the protein is in an amount of between 4 to 8% by weight.

10. Denatured carob flour according to claim 1, wherein the water is in an amount of less than 6% by weight.

11. Foods, dietary supplements, animal feed, pet food, human or animal medicine comprising flour according to claim 1.

12. Denatured carob flour according to claim 1, wherein said cyclitol is pinitol.

13. Process to obtain a flour according to claim 1, comprising the following steps:
    a. cleaning the whole carob fruits;
    b. cruching the whole carob fruits to provide carob seeds and carob pulp;
    c. separating the carob seeds and the carob pulp;
    d. toasting the separated carob pulp between 130° C. and 20° C.;
    e. extracting the toasted carob pulp with water or solvent to remove sugars and water-soluble tannins;
    f. separating the soluble components out of the extracted carob Pulp to produce insoluble residue;
    g. milling the insoluble residue into a powder comprising particles in which 90% of said particles exhibit a particle size below 250 μm;
    h. removing water from the insoluble residue;
    i. drying the milled insoluble residue to a water content of below 8% by weight and
    j. sieving the dried product.

14. Process according to claim 13, wherein in step b, the carob fruit is shredded into pieces smaller than 3 cm.

15. Process according to claim 13, wherein the toasting temperature is between 140 and 150° C.

16. Process according to claim 13, wherein the time period for toasting is between 5 minutes and 60 minutes.

17. Process according to claim 16, wherein the time period for toasting is between 10 minutes and 20 minutes.

18. Process according to claim 13, wherein in step e, the extraction is performed at a temperature in the range of 5 to 80° C.

19. Process according to claim 13, wherein the extraction of step e, is performed with water and the ratio of pulp to water is 1:20 (wt./wt).

20. Process according to claim 13, wherein in step e, the extraction is performed for 5 minutes to 24 hours.

21. Process according to claim 13, wherein in step g, 90% of particles have a article size below 150 μm.

22. Process according to claim 1, wherein between steps g, and h, steps e, and f are, are repeated at least once.

23. Process according to claim 13, wherein in step i, the drying is performed at a temperature which does not exceed 140° C.

24. Process according to claim 13, wherein the process is carried out continuously.

25. Process according to claim 13, wherein said process comprises a total of three extractions and imparts a sugar content within the resulting carob flour of less than 10%.

26. Toasted carob flour comprising sugars in an amount of 2 to 15% by weight, cyclitols in an amount of 0.2 to 1.5% by weight, lignins in an amount of 2 to 10% by weight, celluloses in an amount of 10 to 30% by weight, hemicelluloses in an amount of 3 to 20% by weight, pectins in an amount of 1 to 6% by weight, denatured condensed tannins in an amount of 25 to 55% by weight, protein in an amount of 3 to 9% by weight and water in an amount of less than 8% by weight, wherein said denatured condensed tannins are formed by a heat treatment of from 140 to 200° C., and an effective amount of said toasted carob fiber induces a lower serum cholesterol level than a comparable amount of natural carob fiber.

* * * * *

UNITED STATES PATENT AND TRADEMARK OFFICE
CERTIFICATE OF CORRECTION

PATENT NO.        : 7,393,551 B2                                                Page 1 of 1
APPLICATION NO.   : 10/522512
DATED             : July 1, 2008
INVENTOR(S)       : Ruiz-Roso Calvo De Mora et al.

It is certified that error appears in the above-identified patent and that said Letters Patent is hereby corrected as shown below:

Column 5

Claim 3, Line 22, delete "is"
Claim 3, Line 22, delete "3" insert --0.3--
Claim 13, Line 47, delete "cruching" insert --crushing--
Claim 13, Line 51, delete "20" insert --200--

Column 6

Claim 19, Line 23, delete "(wt./wt)" insert --wt./wt--
Claim 21, Line 27, delete "article" insert --particle--
Claim 22, Line 29, delete "are,"

Signed and Sealed this

Thirtieth Day of December, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,393,551 B2 |
| APPLICATION NO. | : 10/522512 |
| DATED | : July 1, 2008 |
| INVENTOR(S) | : Ruiz-Roso Calvo De Mora et al. |

It is certified that error appears in the above-identified patent and that said Letters Patent is hereby corrected as shown below:

Column 6
Claim 22, Line 28, delete "claim 1" insert --claim 13--

Signed and Sealed this

Ninth Day of June, 2009

JOHN DOLL
*Acting Director of the United States Patent and Trademark Office*